United States Patent
Dehn et al.

(10) Patent No.: US 8,937,207 B2
(45) Date of Patent: Jan. 20, 2015

(54) USE OF SUPPORTED RUTHENIUM-CARBENE COMPLEXES IN CONTINUOUSLY OPERATED REACTORS

(76) Inventors: Richard Dehn, Ludwigshafen (DE); Stephan Deuerlein, Ludwigshafen (DE); Manuel Danz, Plankstadt (DE); Michael Limbach, Worms (DE); Joaquim Henrique Teles, Waldsee (DE)

( * ) Notice: Subject to any disclaimer, the term of this patent is extended or adjusted under 35 U.S.C. 154(b) by 139 days.

(21) Appl. No.: 13/331,384

(22) Filed: Dec. 20, 2011

(65) Prior Publication Data

US 2012/0165588 A1 Jun. 28, 2012

Related U.S. Application Data

(60) Provisional application No. 61/425,782, filed on Dec. 22, 2010.

(51) Int. Cl.
*C07C 6/02* (2006.01)
*C07C 6/04* (2006.01)
*C07C 6/06* (2006.01)

(52) U.S. Cl.
CPC .............. *C07C 6/06* (2013.01); *C07C 2101/00* (2013.01); *C07C 2521/08* (2013.01); *C07C 2531/22* (2013.01)
USPC ................................ 585/601; 585/21; 585/22

(58) Field of Classification Search
CPC ................ C07C 6/00; C07C 6/02; C07C 6/04
USPC ............................................. 585/601, 21, 22
See application file for complete search history.

(56) References Cited

U.S. PATENT DOCUMENTS

| | | | |
|---|---|---|---|
| 6,921,735 B2 | 7/2005 | Hoveyda et al. | |
| 2003/0065234 A1 | 4/2003 | Wohrle et al. | |
| 2005/0043541 A1* | 2/2005 | Walter et al. ................ | 548/101 |
| 2011/0009621 A1 | 1/2011 | Bannwarth et al. | |
| 2011/0294971 A1* | 12/2011 | Jones et al. ................ | 526/171 |

FOREIGN PATENT DOCUMENTS

| | | |
|---|---|---|
| EP | 1288181 A2 | 3/2003 |
| WO | WO-2007065907 A1 | 6/2007 |
| WO | WO-2010021740 A1 | 2/2010 |
| WO | WO 2010021740 A1 * | 2/2010 |

OTHER PUBLICATIONS

D Trong On, D Desplantier-Giscard, C Danumah, S Kaliaguine, Perspectives in catalytic applications of mesostructured materials, Applied Catalysis A: General, vol. 253, Issue 2, Oct. 28, 2003, pp. 545-602, ISSN 0926-860X, http://dx.doi.org/10.1016/S0926-860X(03)00195-9. (http://www.sciencedirect.com/science/article/pii/S0926860X03001959).*
Van Berlo et al., "Silica immobilized Second Generation Hoveyda-Grubbs: A Convenient, Recyclable and Storageable Heterogeneous Solid Catalyst", Adv. Synth. Catal., vol. 350, (2005), pp. 1949-1953.*
Alcaide, B., et al., "Grubbs' Ruthenium-Carbenes Beyond the Metathesis Reaction: Less Conventional Non-Metathetic Utility", Chem. Rev., vol. 109, (2009), pp. 3817-3858.
Balcar, H., et al., "$RuCl_2$($p$-cymene)($PCy_3$) immobilized on mesoporous molecular sieves as catalyst for Romp of norbornene and its derivatives", Journal of Molecular Catalysis A: Chemical, vol. 332, (2010), pp. 19-24.
Ek, S., et al., "Determination of the hydroxyl group content in silica by thermogravimetry and a comparison with $^1H$ MAS NMR results", Thermochimica Acta, vol. 379, (2001), pp. 201-212.
International Search Report (German) for PCT/EP2011/072860, dated Mar. 2, 2012.
Mrowiec-Bialon, J., "Determination of hydroxyls density in the silica-mesostructured cellular foams by thermogravimetry", Thermochimica Acta, vol. 443, (2006), pp. 49-52.
On, D.T., et al., "Perspectives in catalytic applications of mesostructured materials", Applied Catalysis A: General, vol. 253, (2003), pp. 545-602.
Polarz, S., et al., "Metathesis catalysts in confining reaction fields-confinement effects vs.surface effects", Dalton Transactions, vol. 39, (2010), pp. 577-584.
Van Berlo, B., et al., "Silica Immobilized Second Generation Hoveyda-Grubbs: A Convenient, Recyclable and Storageable Heterogeneous Solid Catalyst", Adv. Synth. Catal., vol. 350, (2008), pp. 1949-1953.

* cited by examiner

*Primary Examiner* — In Suk Bullock
*Assistant Examiner* — Philip Louie
(74) *Attorney, Agent, or Firm* — Drinker Biddle & Reath LLP

(57) ABSTRACT

The present invention relates to a process for carrying out a chemical reaction in the presence of a ruthenium-carbene complex supported on silicon dioxide in a continuously operated reactor and also the use of corresponding supported catalysts in continuously operated reactors.

8 Claims, No Drawings

USE OF SUPPORTED RUTHENIUM-CARBENE COMPLEXES IN CONTINUOUSLY OPERATED REACTORS

CROSS-REFERENCE TO RELATED APPLICATIONS

This application claims benefit under 35 U.S.C. §119(e) of U.S. Provisional Patent App. Ser. No. 61/425,782, filed Dec. 22, 2010, which is incorporated herein by reference in its entirety.

The present invention relates to a process for carrying out a chemical reaction in the presence of a ruthenium-carbene complex supported on silicon dioxide in a continuously operated reactor and also the use of corresponding supported catalysts in continuously operated reactors.

The importance of metal-carbene complexes in organic synthetic chemistry, in particular in olefin metathesis, has been emphasized by the award of the Nobel Prize for chemistry to Y. Chauvin, R. R. Schrock and R. H. Grubbs in 2005.

The ruthenium-carbene complexes developed by Grubbs have been found to be significantly less sensitive to oxygen and water than the molybdenum-carbene complexes developed by Schrock, and the ruthenium-carbene complexes are therefore being intensively studied at present in research laboratories in universities and in industry. The most important field of application for ruthenium-carbene complexes is at present olefin metathesis.

Olefin metathesis enables two C—C double bonds to be reacted with one another to form two new C—C double bonds. This type of reaction can be used both industrially, for example in the Shell Higher Olefin Process (SHOP), and in the field of fine chemicals, for example in the synthesis of intermediates for the preparation of flavor chemicals and fragrances.

EP 1 288 181 discloses a process for preparing cycloalkadienes in a metathesis reaction in which supported catalysts based on $Re_2O_7$/gamma-$Al_2O_3$ are used. The cycloalkadienes obtained serve as intermediates for the preparation of fragrances. Disadvantages are the complicated production of the catalyst, carbonization problems, rapid catalyst deactivation and the very complicated catalyst regeneration.

U.S. Pat. No. 6,921,735 describes recoverable ruthenium-carbene complexes. It also discloses, inter alia, the synthesis of a ligand system which has a —$SiMe_2$-Cl unit which in turn can react with a silanol group of a silica gel surface, so that it is ultimately possible to synthesize ruthenium-carbene complexes which are covalently bound via one of their ligands to the surface of a silica gel.

In Adv. Synth. Catal. 2008, 350, 1949-1953, Sels et al. describe a simple process for immobilizing ruthenium-carbene complexes on silica gels and the use of the supported catalysts in various olefin metathesis reactions.

The above-described catalyst systems are not yet optimal in terms of their economics in industrial processes, for example because the costs of catalyst production are too high or because the operating lives of the catalysts in continuously operated processes are not yet satisfactory.

In the light of this prior art, it was an object of the invention to discover economically advantageous processes for carrying out chemical reactions using supported ruthenium-carbene complexes and also to identify catalyst systems based on supported ruthenium-carbene complexes which are suitable for such processes.

This object is achieved by a process for carrying out a chemical reaction in the presence of a supported catalyst comprising at least one ruthenium-carbene complex as catalytically active component and a silicon dioxide as support material, wherein the silicon dioxide used for producing the supported catalyst has a ratio of OH groups on its surface to the $N_2$ BET surface area which is less than 2 OH groups/$nm^2$ and the chemical reaction is carried out in a continuously operated reactor.

In the process of the invention, various chemical reactions can be carried out in the presence of the above-specified supported catalyst in a continuously operated reactor. Examples of such reactions catalyzed by ruthenium-carbene complexes are olefin metathesis, free-radical additions of tetrachloromethane or chloroform onto terminal double bonds (atom transfer radical addition), the free-radical 5-exo-trig-cyclization of diallyl systems (atom transfer radical cyclization) or the activation of silanes to produce silyl ethers or the hydrosilylation of carbonyl compounds. A comprehensive overview of the use of Ru-carbenes in organic synthesis may be found in: Alcaide, B.; Almendros, P; Luna, A., Chem. Rev. 2009, 109, 3817-3858.

The chemical reaction in the process of the invention is preferably an olefin metathesis.

The term olefin metathesis refers to the transalkylidenation of two olefinic double bonds in the presence of a transition metal catalyst. The important types of reaction are cross metathesis, ring-closure metathesis, ring-opening cross metathesis, ring-opening metathesis polymerization and the metathetic polymerization of acyclic dienes. A comprehensive but not conclusive overview may be found, for example, in:

a) Ivin, K. J.; Mol, J. C., "Olefin Metathesis and Metathesis Polymerization", Academic Press, San Diego, 1997. b) Grubbs, R. H., "Handbook of Metathesis", Wiley VCH, 1st edition, Weinheim, 2003.

The chemical reaction in the process of the invention is accordingly, in particular, a cross metathesis, ring-closure metathesis, ring-opening cross metathesis, ring-opening metathesis polymerization or the metathetic polymerization of acyclic dienes.

A particularly preferred type of olefin metathesis reaction is the dimerization and trimerization of cyclic olefins to form cylic dienes or cyclic trienes, in particular the dimerization of cyclic olefins to form cylic dienes.

The chemical reaction carried out in the process of the invention is particularly preferably the preparation of cycloalkadienes from cycloalkene monomers, polycycloalkenylenes or mixtures of the two.

Possible cycloalkene monomers are, for example, cyclopentene, cycloheptene, cyclooctene and higher cycloalkenes. Particular preference is given to cyclopentene and cyclooctene, in particular cyclooctene.

The cycloalkadienes of the general formula $C_{2n}H_{4n-4}$ are preferably dimers formed from two molecules of a cycloalkene monomer of the general formula $C_nH_{2n-2}$, where n is from 5 to 20, preferably from 6 to 15, particularly preferably from 7 to 10, in particular 8.

Since olefin metathesis is a reversible reaction, the cycloalkadienes of the general formula $C_{2n}H_{4n-4}$ can also be obtained by backreaction of the corresponding polycycloalkenylenes of the general formula $(C_nH_{2n-2})_m$, where m is an integer greater than or equal to 3 and n is as defined above.

The process of the present invention is very particularly preferably a process for preparing 1,9-cyclohexadecadiene ($C_{16}H_{28}$) from cyclooctene ($C_8H_{14}$), polycyclooctenylene $((C_nH_{2n-2})_m)$ or mixtures of the two.

The process of the invention can usually, depending on the type of reaction and starting compounds used, be carried out in a temperature range from −50° C. to 200° C. Olefin metathesis is preferably carried out in a temperature range from 0° C. to 200° C.

The process of the invention can, depending on the type of reaction and starting compounds used, be carried out with or without solvent. In the case of olefin metathesis, the process of the invention is preferably carried out in a solvent or solvent mixture which is inert toward the metathesis catalyst. Examples of such inert solvents are, inter alia, aromatic hydrocarbons (benzene, toluene, xylene, etc.), halogenated aromatic hydrocarbons, aliphatic hydrocarbons (pentane, hexane, cyclopentane, cyclohexane, etc.), chlorinated aliphatics (dichloromethane, dichloroethane, etc.) and mixtures thereof. The process of the invention is particularly preferably carried out in aromatic or aliphatic hydrocarbons, in particular in alkanes such as n-heptane or cycloalkanes such as cyclohexane.

Despite the relative insensitivity of the ruthenium-carbene complexes used to water and oxygen, the process of the invention is preferably carried out using ideally water-free solvents and starting compounds and also with exclusion of atmospheric oxygen, preferably under a protective gas atmosphere, for example dry nitrogen or argon.

The supported catalyst used in the process of the invention comprises at least one ruthenium-carbene complex as catalytically active component and a silicon dioxide as support material.

Ruthenium-carbene complexes comprise at least one ruthenium-carbon double bond as central fragment of the complex and belong to the class of metal-alkylidene complexes. Apart from mononuclear complexes, viz. those having one ruthenium atom, there are also binuclear or multinuclear complexes, namely those having two or more ruthenium atoms.

Ruthenium-carbene complexes which are suitable according to the invention are described, for example, in WO 2010/021740, page 15, paragraph 0066 to page 27, paragraph 00102; the cited document is incorporated by reference in its entirety into the present disclosure.

Preference is given to a process according to the invention in which the ruthenium-carbene complex is a compound of the formula (I),

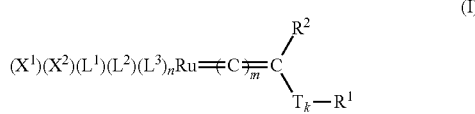

where
$X^1$, $X^2$ can be identical or different and are each an anionic ligand,
$L^1$, $L^2$, $L^3$ can be identical or different and are each an uncharged electron donor ligand,
T is O, S, $NR^{11}$ or $PR^{11}$,
$R^{11}$ is hydrogen or a $C_1$-$C_{40}$ radical,
$R^1$, $R^2$ can be identical or different and are each hydrogen or a $C_1$-$C_{40}$ radical,
   or two or more of the ligands or radicals selected from the group consisting of $X^1$, $X^2$, $L^1$, $L^2$, $L^3$, $R^1$ and $R^2$ are joined to one another and form a cyclic or polycyclic ring system,
k is 0 or 1,
n is 0 or 1 and
m is 0, 1 or 2.

$X^1$, $X^2$ can be identical or different, in particular identical, and are each an anionic ligand. $X^1$, $X^2$ are preferably halogen, for example fluorine, chlorine, bromine, iodine, preferably chlorine, or pseudohalogen, for example cyano, thiocyano, etc., or methyl, phenyl, aryloxy or alkoxy. $X^1$ and $X^2$ are particularly preferably chlorine.

$L^1$, $L^2$, $L^3$ can be identical or different and are each an uncharged electron donor ligand. Preferred uncharged electron donor ligands are described in WO 2010/021740, page 16, paragraph 0070 and page 17, paragraph 0075; the cited document is incorporated by reference in its entirety into the present disclosure. Particularly preferred uncharged electron donor ligands are carbenes stabilized by two atoms of group 15 or 16 of the Periodic Table of the Elements, in particular by two nitrogen atoms (known as Arduengo carbenes), and also ethers, thioethers, amines or nitrogen-comprising heterocycles, in particular pyridine or pyridine derivatives.

T is O, S, $NR^{11}$ or $PR^{11}$, preferably S or $NR^{11}$.

$R^{11}$ is hydrogen or a $C_1$-$C_{40}$ radical, for example $C_1$-$C_{20}$-alkyl, $C_2$-$C_{20}$-alkenyl, $C_2$-$C_{20}$-alkynyl, $C_6$-$C_{40}$-aryl, $C_7$-$C_{40}$-alkylaryl, $C_7$-$C_{40}$-arylalkyl, $C_2$-$C_{40}$-heteroaromatic radical, saturated $C_3$-$C_{20}$-heterocyclic radical or silyl radical having from 3 to 24 carbon atoms, where the carbon-comprising radical can comprise further heteroatoms selected from the group of elements consisting of F, Cl, Br, I, N, P, O and S and/or be substituted by functional groups.

$R^1$, $R^2$ can be identical or different and are each hydrogen or a $C_1$-$C_{40}$ radical, for example $C_1$-$C_{20}$-alkyl, $C_2$-$C_{20}$-alkenyl, $C_2$-$C_{20}$-alkynyl, $C_6$-$C_{40}$-aryl, $C_7$-$C_{40}$-alkylaryl, $C_7$-$C_{40}$-arylalkyl, $C_2$-$C_{40}$-heteroaromatic radical, saturated $C_3$-$C_{20}$-heterocyclic radical or silyl radical having from 3 to 24 carbon atoms, where the carbon-comprising radical can comprise further heteroatoms selected from the group of elements consisting of F, Cl, Br, I, N, P, O and S and/or be substituted by functional groups.

Two or more of the ligands or radicals selected from the group consisting of $X^1$, $X^2$, $L^1$, $L^2$, $L^3$ $R^1$ and $R^2$ can also be joined to one another and form a cyclic or polycyclic ring system. Preference is given to precisely one of the radicals $L^1$, $L^2$ or $L^3$ being joined to precisely one of the radicals $R^1$ or $R^2$ to form, together, a cyclic or polycyclic ring system.

n is 0 or 1, preferably 0, and m is 0, 1 or 2, preferably 0.

The process of the invention is particularly preferably carried out using a ruthenium-carbene complex of the formula (I) in which the uncharged electron donor ligand $L^1$ is a carbene of the formula (II),

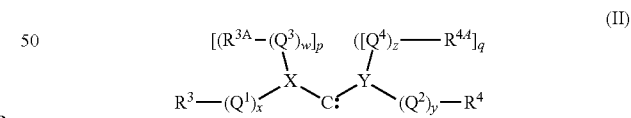

where
X, Y can be identical or different, preferably identical, and are each a heteroatom selected from the group of elements consisting of N, O, S and P, preferably N,
p is 0 when X is O or S, and p is 1 when X is N or P,
q is 0 when Y is O or S, and p is 1 when Y is N or P,
$Q^1$, $Q^2$, $Q^3$, $Q^4$ are each, independently of one another, a divalent organic group having from 1 to 40 carbon atoms, where, in addition, two or more substituents on adjacent atoms within $Q^1$, $Q^2$, $Q^3$ and/or $Q^4$ can be joined to one another to form an additional cyclic or polycyclic structure,
w, x, y, z are each, independently of one another, 0 or 1, preferably all 0, and $R^3$, $R^{3A}$, $R^4$ and $R^{4A}$ can be identical or different and are each, independently of one another, hydrogen or a $C_1$-$C_{40}$ radical.

$R^3$, $R^{3A}$, $R^4$ and $R^{4A}$ can be identical or different and are each, independently of one another, hydrogen or a $C_1$-$C_{40}$ radical, for example $C_1$-$C_{20}$-alkyl, $C_2$-$C_{20}$-alkenyl, $C_2$-$C_{20}$-alkynyl, $C_5$-$C_{40}$-aryl, $C_7$-$C_{40}$-alkylaryl, $C_7$-$C_{40}$-arylalkyl, $C_2$-$C_{40}$-heteroaromatic radical, saturated $C_3$-$C_{20}$-heterocyclic radical or silyl radical having from 3 to 24 carbon atoms, where the carbon-comprising radical can comprise further heteroatoms selected from the group of elements consisting of F, Cl, Br, I, N, P, O and S and/or be substituted by functional groups.

$Q^1$, $Q^2$, $Q^3$, $Q^4$ are each, independently of one another, a divalent organic group having from 1 to 40 carbon atoms, where, in addition, two or more substituents on adjacent atoms within $Q^1$, $Q^2$, $Q^3$ and/or $Q^4$ can be joined to one another to form an additional cyclic or polycyclic structure. The divalent organic group having from 1 to 40 carbon atoms can be, for example, a divalent hydrocarbon group, a substituted divalent hydrocarbon group, a divalent heteroatom-comprising hydrocarbon group, a substituted and at the same time heteroatom-comprising divalent hydrocarbon group or —(CO)—.

The process of the invention is very particularly preferably carried out using a ruthenium-carbene complex of the formula (I) in which the uncharged electron donor ligand $L^1$ is a carbene of the formula (II)
in which
m is 0,
w, x, y, z are each 0,
p, q are each 1,
X, Y are each N and
$R^{3A}$ and $R^{4A}$ are joined to one another and together form Q, a divalent organic group having from 1 to 40 carbon atoms, where the very particularly preferred ruthenium-carbene complex can be described by the formula (III).

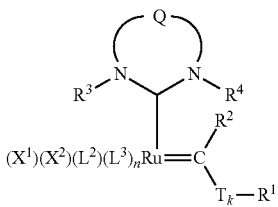

(III)

In the ruthenium-carbene complex of the formula (III), the uncharged electron donor ligand $L^2$ is preferably phosphite, phosphinite, arsane, stibane, ether, amine, amide, imine, sulfoxide, carboxylate, nitrosyl, pyridine, substituted pyridine, imidazole, substituted imidazole, pyrazine, thioether or pyrrolidone.

Q is a divalent organic group having from 1 to 40 carbon atoms. The divalent organic group having from 1 to 40 carbon atoms can be, for example, a divalent hydrocarbon group, a substituted divalent hydrocarbon group, a divalent heteroatom-comprising hydrocarbon group or a substituted and at the same time heteroatom-comprising divalent hydrocarbon group.

In the ruthenium-carbene complex of the formula (III), any combinations of two or more of the groups $X^1$, $X^2$, $L^2$, $L^3$, $R^1$ $R^2$, $R^3$ and $R^4$ can be joined to one another and form cyclic structures.

In particular, the process of the invention is carried out using a ruthenium-carbene complex of the formula (IV),

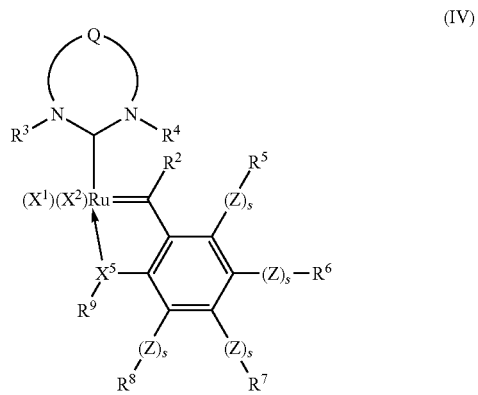

(IV)

where
$X^1$, $X^2$, Q, $R^2$, $R^3$, $R^4$ are as defined for the formulae (I), (II) and (III),
$X^5$ is O, S or $PR^{10}$, preferably O,
Z are each, independently of one another, O, S, $NR^{10}$ or $PR^{10}$, preferably O or $NR^{10}$,
the indices s are each, independently of one another, 0 or 1,
$R^5$, $R^6$, $R^7$, $R^8$, $R^9$ can be identical or different and are each, independently of one another, hydrogen or a $C_1$-$C_{40}$ radical or in the case of s=0 can also be a functional group selected from among $NO_2$, CN, COOH, $COOR^{10}$ and halogen and
the radicals $R^{10}$ can be identical or different and are each, independently of one another, hydrogen or a $C_1$-$C_{40}$ radical.

$R^5$, $R^6$, $R^7$, $R^8$, $R^9$ are identical or different and are each, independently of one another, hydrogen or a $C_1$-$C_{40}$ radical, for example $C_1$-$C_{20}$-alkyl, $C_2$-$C_{20}$-alkenyl, $C_2$-$C_{20}$-alkynyl, $C_6$-$C_{40}$-aryl, $C_7$-$C_{40}$-alkylaryl, $C_7$-$C_{40}$-arylalkyl, $C_2$-$C_{40}$-heteroaromatic radical, saturated $C_3$-$C_{20}$-heterocyclic radical or silyl radical having from 3 to 24 carbon atoms, where the carbon-comprising radical can comprise further heteroatoms selected from the group of elements consisting of F, Cl, Br, I, N, P, O and S and/or be substituted by functional groups or in the case of s=0 can also be a functional group selected from among $NO_2$, CN, COOH, $COOR^{10}$ and halogen, e.g. F, Cl, Br or I.

The radical or radicals $R^{10}$ can be identical or different and are each, independently of one another, hydrogen or a $C_1$-$C_{40}$ radical, for example $C_1$-$C_{20}$-alkyl, $C_2$-$C_{20}$-alkenyl, $C_2$-$C_{20}$-alkynyl, $C_6$-$C_{40}$-aryl, $C_7$-$C_{40}$-alkylaryl, $C_7$-$C_{40}$-arylalkyl, $C_2$-$C_{40}$-heteroaromatic radical, saturated $C_3$-$C_{20}$-heterocyclic radical or silyl radical having from 3 to 24 carbon atoms, where the carbon-comprising radical can comprise further heteroatoms selected from the group of elements consisting of F, Cl, Br, I, N, P, O and S and/or be substituted by functional groups.

The supported catalyst used in the process of the invention comprises the above-described ruthenium-carbene complex together with, as a further component, a silicon dioxide which, before production of the supported catalyst, has a ratio of OH groups on its surface to $N_2$ BET surface area of less than 2 OH groups/nm². Preference is given to the ratio of OH groups to $N_2$ BET surface area on the silicon dioxide used for producing the supported catalyst being less than 1.5 OH groups/nm², in particular from 0.1 to 1.2 OH groups/nm².

The OH density on the support surface can be set by means of any method known to those skilled in the art. Particularly suitable methods for setting the OH density on the support surface are thermal treatment of the support, for example in $N_2$ or air, and optionally under reduced pressure, or chemical reaction of the OH groups on the support surface, for example by reaction of the OH groups on the surface, also referred to as silanol groups, with trimethylsilyl chloride, potassium hexamethyldisilazane or other suitable silylating agents or, for example, by alkylation, in particular methylation using dimethyl sulfate, methyl iodide or other suitable alkylating reagents.

In the process of the invention, the ratio of OH groups to the $N_2$ BET surface area on the surface of the silicon dioxide used is preferably set by thermal treatment of the silicon dioxide. For this purpose, the silicon dioxide is usually dried for a particular time at a temperature of from 200° C. to 1200° C., preferably from 400° C. to 1100° C., until the desired ratio of OH groups to $N_2$ BET surface area has been reached.

The determination of the $N_2$ BET surface area and the determination of the number of OH groups on the surface of the silicon dioxide used are carried out by methods which are known to those skilled in the art and are described in detail in the experimental part.

In the process of the invention, the molar ratio of the OH groups on the surface of the silicon dioxide to the ruthenium-carbene complex used can be varied in a wide range in the production of the supported catalyst.

However, preference is given to a process according to the invention in which the ruthenium-carbene complex is used in such a ratio to the silicon dioxide used in the production of the supported catalyst that the molar ratio of OH groups on the surface of the silicon dioxide to the ruthenium-carbene complex is at least 5, preferably at least 10, in particular at least 20.

Particular preference is given to a silicon dioxide which has not been modified on the surface in such a way that further bonding sites, i.e. sites suitable for a chemical or physical bonding interaction, in addition to the OH groups (silanol groups) are created for the ruthenium-carbene complexes. This explicitly does not encompass silicon dioxides whose OH groups on the surface have merely been passivated or masked as described above, e.g. by reaction with trimethylsilyl chloride or reagents having a similar action.

The silicon dioxides to be used as support material preferably have an $N_2$ BET surface area in the range from 10 to 1000 $m^2/g$, preferably from 300 to 900 $m^2/g$, particularly preferably from 450 to 800 $m^2/g$, and preferably have a pore volume in the range from 0.1 to 5 ml/g, preferably in the range from 0.5 to 3.5 ml/g, with the pores preferably having an average diameter of from 20 to 200 Å, preferably 40-120 Å, in particular from 50 to 70 Å.

The silicon dioxide to be used as support material can in principle be present in various forms, for example as powder having an average particle diameter of from 0.1 to 500 μm or, if technically advantageous, as macroscopic shaped bodies having any shape and preferably having a size of from 0.5 to 10 cm. Such shaped bodies can be, for example: extrudates, spheres, pellets, crushed material, hollow extrudates (rings), etc. Shaped bodies having an ordered structure, e.g. monoliths, can also be used; in this case, sizes up to 30 cm are not a rarity.

The silicon dioxide used in the process of the invention is preferably a silica gel which has been dried.

The process of the invention is particularly preferably carried out using a silicon dioxide which is a dried silica gel which has a ratio of OH groups to $N_2$ BET surface area in the range from 0.1 to 1.2 OH groups/$nm^2$ and whose pores have an average diameter of from 50 to 70 Å and which also, in particular, has an $N_2$ BET surface area of from 450 to 800 $m^2/g$.

The supported catalyst can, for example, be produced by simple combining of a solution of the ruthenium-carbene complex with the silicon dioxide as support material and optionally subsequent filtration, washing and/or drying steps, as described, for example, in Adv. Synth. Catal. 2008, 350, 1949-1953.

Chemical reaction which is carried out in the process of the invention is carried out in a continuously operated reactor.

In a continuous process, starting materials (possibly together with further materials such as solvents, gases, etc.) are fed simultaneously to the reaction space/reactor and a product stream is taken from the reaction space/reactor. A general description of continuous processes and alternative definitions may be found in textbooks on chemical process engineering (e.g. E. Fitzner, W. Fritz, E. Klemm "Technische Chemie: Einführung in die chemische Reaktionstechnik", 2005, 5th edition, Springer, Berlin-ISBN 3540234527). Reactors which are particularly suitable for continuous processes are, for example, tube reactors, continuously operated stirred vessels or cascades thereof, etc. Here too, a comprehensive description may be found in the cited literature.

The process of the invention is preferably carried out in a tube reactor, a shell-and-tube reactor or a cascade of continuously operated stirred vessels, particularly preferably in a tube reactor or shell-and-tube reactor.

In the process of the invention, the total amount of starting material passed through the reaction space during the life/operating life of the catalyst is preferably 20 times, particularly preferably 100 times, in particular 1000 times, the mass of the supported catalyst itself.

In the case of the dimerization of cyclic olefins to form cylic dienes in the process of the invention, the reaction in the continuously operated reactor is preferably carried out so that the proportion by weight of cyclic dienes, based on the total mass of cyclic olefin, cyclic diene and polymer, in the reaction mixture discharged is more than 10%, particularly preferably in the range from 20 to 50%.

The invention further provides for the use of a supported catalyst comprising at least one ruthenium-carbene complex as catalytically active component and a silicon dioxide as support material, with the silicon dioxide used for producing the supported catalyst having a ratio of OH groups on its surface to $N_2$ BET surface area of less than 2 OH groups/$nm^2$, as heterogeneous catalyst system in a chemical reaction carried out in a continuously operated reactor.

Preferred embodiments in respect of the ruthenium-carbene complex, the silicon dioxide, the chemical reaction and the continuously operated reactor have been discussed above in connection with the process of the invention and can be applied in the same way to the use according to the invention of a supported catalyst.

The invention is illustrated by the following examples which do not, however, restrict the invention.

Support:

The silica gels GD SP550 10012 and 10020, having an average pore diameter of 30 and 60 Å, respectively, were obtained from Grace Davison. The microporous support D11-10 is a commercial product of BASF SE. The mesoporous material MCM-41 (average pore diameter 180 Å) was synthesized in-house by a literature method (V. Mynen, P. Cool, E. F. Vansant "Verified syntheses of mesoporous materials" Micropor. Mesopor. Mater. 2009, 125, 170-223, 6.4). The same literature reference also gives details of the structure type MCM-41 and indicates further literature.

Preparation of the Support:

To calcine the material, it was brought to the desired temperature $T_{calc.}$ at a heating rate of 2° C./min under a nitrogen atmosphere, maintained at that temperature for 4 hours and subsequently cooled to room temperature. The support was calcined immediately before the impregnation step (see below) and was handled only under $N_2$ after the calcination.

Analysis of the Support:

Determination of the $N_2$ BET Surface Area:

The determination of the $N_2$ BET surface area was carried out by means of $N_2$ adsorption in accordance with DIN ISO 9277:2003-05 "Bestimmung der spezifischen Oberfläche von Feststoffen durch Gasadsorption nach dem BET-Verfahren" (ISO 9277:1995, publication date May 2003).

Determination of the Number of OH Groups on the Support:

The number of OH groups on the surface of the support was determined gravimetrically. For this purpose, the support was heated at 5° C./min to the temperature $T_{calc.}$ corresponding to the calcination of the support and maintained at this temperature for 4 hours. The support was subsequently heated further to 1200° C. at 5° C./min. The change in mass occurring during the second heating phase was detected. The water liberated in the range from the temperature to be examined to 1200° C. originated from the condensation of OH groups on the support surface. Every two Si—OH units form one water molecule and crosslink to form an Si—O—Si unit. The loss in weight of the support is thus related as follows to the number of condensed OH groups:

$$\frac{\text{Number(OH)}}{m(\text{Sample})} = 2\frac{\Delta m}{M(H_2O)}\frac{N_A}{m(\text{Sample})} \text{ with the unit } \frac{1}{g}$$

Calculation of the OH Density of the Support:

The number of OH groups divided by the mass of support at $T_{calc.}$ and $N_2$ BET surface area of the support (BET for short) gives the OH density of the support:

$$\text{OH} - \text{Density}(T_{calc.}) = \frac{\text{Number(OH)}}{m(\text{Sample})\ BET} \text{ with the unit } \frac{1}{nm^2}$$

Method of Determining the Porosity of Solids:

The porosity of the support was determined in accordance with DIN ISO 66133 "Bestimmung der Porenvolumenverteilung and der spezifischen Oberfläche von Feststoffen durch Quecksilberintrusion" (publication date June 1993-06).

Results for the Supports Used:

Support According to the Invention:

GD SP550 10020-1.2 OH/nm² at 550° C.-0.4 OH/nm² at 850° C.

MCM-41-1.6 OH/nm² at 550° C.

Support not According to the Invention:

D11-10-5.5 OH/nm² at 550° C.

GD SP550 10012-7.0 OH/nm² at 550° C.

GD SP550 10020-3.5 OH/nm² uncalc.

The Ru complex 1 used in the examples is the ruthenium complex of the formula (a)

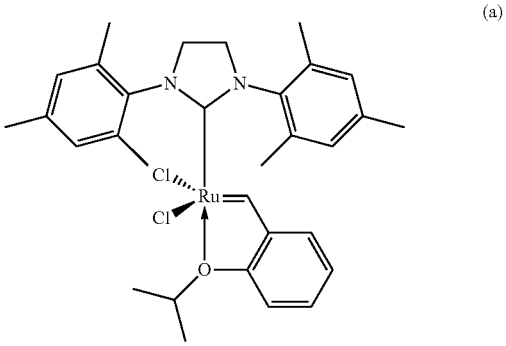

(a)

EXAMPLES

Preliminary remark: the feed stream was passed over a purification bed comprising 4 Å molecular sieves to remove water and over a purification bed comprising R3-11G absorber (BASF SE) to remove oxygen compounds before coming into contact with the catalyst.

Example 1

Production of the Catalyst:

Silica gel from Grace (type SP550-10020 ID 4907) was calcined at 550° C. under a gentle stream of nitrogen in a fused silica tube for 4 hours. The OH density on the surface of the support was measured and was 1.2 OH groups/nm². To produce the heterogeneous catalyst, 20 g of the silica obtained in this way were suspended in dichloromethane and 81 mg of Ru complex 1 were added. The suspension was swirled for 2 hours and the solvent was subsequently removed under reduced pressure. The solid obtained was green and comprised 67 mg of Ru/100 g of catalyst.

Metathesis Reaction:

A vertical tube reactor (diameter: 14 mm, length: 45 cm) was firstly charged in a countercurrent of inert gas with about 20 g of the supported catalyst produced above and the reactor volume above this was filled with glass beads. A solution of cyclooctene in cyclohexane (0.7% by weight) was passed continuously from the bottom upward through the bed at 60° C. and slightly superatmospheric pressure, with a flow rate of 8 ml of feed per minute being set. The conversion at the beginning of the experiment was >90% at a selectivity of 20-25% to 1,9-cyclohexadecadiene. The total selectivity to polycyclooctenylenes was >99%. After 90 hours, the conversion of cyclooctene was still about 75%.

Example 2

Production of the Catalyst:

Silica gel from Grace (type SP550-10020 ID 4907) was calcined at 850° C. under a gentle stream of nitrogen in a fused silica tube for 4 hours. The OH density on the surface of the support was measured and was 0.4 OH groups/nm². To produce the heterogeneous catalyst, 20 g of the silica obtained in this way were suspended in dichloromethane and 81 mg of Ru complex 1 were added. The suspension was swirled for 2 hours and the solvent was subsequently removed under reduced pressure. The solid obtained was green and comprised 68 mg of Ru/100 g of catalyst.

Metathesis Reaction:

A vertical tube reactor (diameter: 14 mm, length: 45 cm) was firstly charged in a countercurrent of inert gas with about 20 g of the supported catalyst produced above and the reactor volume above this was filled with glass beads. A solution of cyclooctene in cyclohexane (0.7% by weight) was passed continuously from the bottom upward through the bed at 60° C. and slightly superatmospheric pressure, with a flow rate of 8 ml of feed per minute being set. The conversion at the beginning of the experiment was >90% at a selectivity of 20-25% to 1,9-cyclohexadecadiene. The total selectivity to polycyclooctenylenes was >99%. After 175 hours, the conversion of cyclooctene was still about 75%.

Example 3

Production of the Catalyst:

15 g of silica gel of the type MCM-41 (the OH density on the surface of the support was measured and was 1.6 OH groups/nm$^2$) were suspended in dichloromethane and 83 mg of Ru complex 1 were added. The suspension was swirled for 2 hours and the solvent was subsequently removed under reduced pressure. The solid obtained was green and comprised 111 mg of Ru/100 g of catalyst.

Metathesis Reaction:

A vertical tube reactor (diameter: 14 mm, length: 45 cm) was firstly charged in a countercurrent of inert gas with about 15 g of the supported catalyst produced above and the reactor volume above this was filled with glass beads. A solution of cyclooctene in cyclohexane (0.7% by weight) was passed continuously from the bottom upward through the bed at 60° C. and slightly superatmospheric pressure, with a flow rate of 8 ml of feed per minute being set. The conversion at the beginning of the experiment was >90% at a selectivity of 20-25% to 1,9-cyclohexadecadiene. The total selectivity to polycyclooctenylenes was >99%. After 10 hours, the conversion of cyclooctene was still about 75%.

Comparative Example 4

Production of the Catalyst:

20 g of silica gel from Grace (type SP550-10020 ID 4907, OH density on the surface of the support was measured and was 3.5 OH groups/nm$^2$) were suspended in dichloromethane and 83 mg of Ru complex 1 were added. The suspension was swirled for 2 hours and the solvent was subsequently removed under reduced pressure. The solid obtained was green and comprised 63 mg of Ru/100 g of catalyst.

Metathesis Reaction:

A vertical tube reactor (diameter: 14 mm, length: 45 cm) was firstly charged in a countercurrent of inert gas with about 20 g of the supported catalyst produced above and the reactor volume above this was filled with glass beads. A solution of cyclooctene in cyclohexane (0.7% by weight) was passed continuously from the bottom upward through the bed at 60° C. and slightly superatmospheric pressure, with a flow rate of 8 ml of feed per minute being set. The conversion at the beginning of the experiment was 65% at a selectivity of 20-25% to 1,9-cyclohexadecadiene. After about 7 hours, the conversion was less than 10%.

Comparative Example 5

Production of the Catalyst:

Silica gel from Grace (type SP550-10012 ID 4906) was calcined at 550° C. under a gentle stream of nitrogen in a fused silica tube for 4 hours. The OH density on the surface of the support was measured and was 7.0 OH groups/nm$^2$. To produce the heterogeneous catalyst, 28 g of the silica obtained in this way were suspended in dichloromethane and 83 mg of Ru complex 1 were added. The suspension was swirled for 2 hours and the solvent was subsequently removed under reduced pressure. The solid obtained was green and comprised 46 mg of Ru/100 g of catalyst.

Metathesis Reaction:

A vertical tube reactor (diameter: 14 mm, length: 45 cm) was firstly charged in a countercurrent of inert gas with about 20 g of the supported catalyst produced above and the reactor volume above this was filled with glass beads. A solution of cyclooctene in cyclohexane (0.7% by weight) was passed continuously from the bottom upward through the bed at 60° C. and slightly superatmospheric pressure, with a flow rate of 8 ml of feed per minute being set. The conversion at the beginning of the experiment was >80% at a selectivity of 20-25% to 1,9-cyclohexadecadiene. After about 7 hours, the conversion was less than 40%.

Comparative Example 6

Production of the Catalyst:

34.5 g of silica gel from BASF (type D11-10; the OH density on the surface of the support was measured and was 7.4 OH groups/nm$^2$) were suspended in dichloromethane and 160 mg of Ru complex 1 were added. The suspension was swirled for 2 hours and the solvent was subsequently removed under reduced pressure. The solid obtained was green and comprised 72 mg of Ru/100 g of catalyst.

Metathesis Reaction:

A vertical tube reactor (diameter: 14 mm, length: 45 cm) was firstly charged in a countercurrent of inert gas with about 20 g of the supported catalyst produced above and the reactor volume above this was filled with glass beads. A solution of cyclooctene in cyclohexane (0.7% by weight) was passed continuously from the bottom upward through the bed at 60° C. and slightly superatmospheric pressure, with a flow rate of 16 ml of feed per minute being set. The conversion at the beginning of the experiment was >25% at a selectivity of 25-35% to 1,9-cyclohexadecadiene. After about 7 hours, the conversion was less than 5%.

The invention claimed is:

1. An olefin metathesis process comprising
reacting cycloalkene monomers, polycycloalkenylenes, or mixtures of the two, in the presence of a supported catalyst comprising at least one ruthenium-carbene complex as a catalytically active component and a silicon dioxide support material,
wherein the silicon dioxide support material has a ratio of OH groups on its surface to N$_2$ BET surface area of less than 2 OH groups/nm$^2$,
wherein the reaction produces cycloalkadienes,
and wherein the reaction is carried out in a continuously operated reactor, such that the total amount of starting material passed through a reaction space during the life/operating life of the catalyst is at least 20 times the mass of the supported catalyst itself.

2. The process according to claim 1, wherein the ruthenium-carbene complex is a compound of the formula (I),

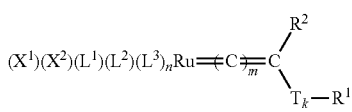 (I)

where
- $X^1$, $X^2$ can be identical or different and are each an anionic ligand,
- $L^1$, $L^2$, $L^3$ can be identical or different and are each an uncharged electron donor ligand,
- T is O, S, $NR^{11}$ or $PR^{11}$,
- $R^{11}$ is hydrogen or a $C_1$-$C_{40}$ radical,
- $R^1$, $R^2$ can be identical or different and are each hydrogen or a $C_1$-$C_{40}$ radical, or two or more of the ligands or radicals selected from the group consisting of $X^1$, $X^2$, $L^1$, $L^2$, $L^3$, $R^1$ and $R^2$ are joined to one another and form a cyclic or polycyclic ring system,
- k is 0 or 1,
- n is 0 or 1 and
- m is 0, 1 or 2.

3. The process according to claim 1, wherein the ratio of OH groups to $N_2$ BET surface area on the surface of the silicon dioxide is set by thermal treatment of the silicon dioxide.

4. The process according to claim 1, wherein the supported catalyst has a molar ratio of OH groups on the surface of the silicon dioxide to the ruthenium-carbene complex of at least 5.

5. The process according to claim 1, wherein the silicon dioxide support material is a dried silica gel having a ratio of OH groups to $N_2$ BET surface area in the range of 0.1 to 1.2 OH groups/nm$^2$ and an average pore diameter of 50 to 70 Å.

6. The process according to claim 1, wherein the supported catalyst is produced by combining a solution of the ruthenium-carbene complex with the silicon dioxide.

7. The process according to claim 1, wherein the supported catalyst is produced by combining a solution of the ruthenium-carbene complex with the silicon dioxide and filtering, washing, and drying, the resulting composition.

8. The process according to claim 1, wherein the supported catalyst is produced by combining a solution of the ruthenium-carbene complex with the silicon dioxide and at least one of filtering, washing, or drying, the resulting composition.

* * * * *